United States Patent
Banba et al.

(10) Patent No.: US 7,205,133 B2
(45) Date of Patent: Apr. 17, 2007

(54) PROCESS FOR PRODUCING ACRYLAMIDE USING A MICROBIAL CATALYST HAVING BEEN WASHED WITH AQUEOUS ACRYLIC ACID SOLUTION

(75) Inventors: Hiroyasu Banba, Kanagawa (JP); Natsuko Morooka, Kanagawa (JP)

(73) Assignee: Dia-Nitrix Co., Ltd., Tokyo (JP)

( * ) Notice: Subject to any disclaimer, the term of this patent is extended or adjusted under 35 U.S.C. 154(b) by 373 days.

(21) Appl. No.: 10/472,482

(22) PCT Filed: Mar. 27, 2002

(86) PCT No.: PCT/JP02/02990

§ 371 (c)(1),
(2), (4) Date: Sep. 29, 2003

(87) PCT Pub. No.: WO02/077253

PCT Pub. Date: Oct. 3, 2002

(65) Prior Publication Data

US 2004/0086986 A1 May 6, 2004

(30) Foreign Application Priority Data

Mar. 27, 2001 (JP) .............................. 2001-090715

(51) Int. Cl.
*C12P 13/02* (2006.01)

(52) U.S. Cl. ..................................................... 435/129
(58) Field of Classification Search ................. 435/129
See application file for complete search history.

(56) References Cited

U.S. PATENT DOCUMENTS

| | | | | |
|---|---|---|---|---|
| 4,343,900 A | * | 8/1982 | Watanabe | .................... 435/129 |
| 4,421,855 A | | 12/1983 | Watanabe et al. | |
| 4,555,487 A | * | 11/1985 | Yamada et al. | .......... 435/253.3 |
| 5,179,014 A | * | 1/1993 | Watanabe et al. | ........... 435/129 |
| 5,807,730 A | * | 9/1998 | Ito et al. | ..................... 435/232 |
| 6,043,061 A | | 3/2000 | Ishii et al. | |

FOREIGN PATENT DOCUMENTS

| | | | |
|---|---|---|---|
| JP | 8-266277 | * | 10/1996 |
| JP | 2001-299376 | | 10/2001 |

* cited by examiner

*Primary Examiner*—Leon B. Lankford, Jr.
*Assistant Examiner*—Susan Hanley
(74) *Attorney, Agent, or Firm*—Oblon, Spivak, McClelland, Maier & Neustadt, P.C.

(57) ABSTRACT

Provided is a process for producing acrylamide with good storage stability and improved acrylamide polymer physical properties using a microbial catalyst. A microbial catalyst having catalytic activity to convert from acrylonitrile to acrylamide is washed with an aqueous acrylic acid solution, and then the washed microbial catalyst is used for the conversion reaction, so that the production of the above acrylamide is achieved.

8 Claims, No Drawings

PROCESS FOR PRODUCING ACRYLAMIDE USING A MICROBIAL CATALYST HAVING BEEN WASHED WITH AQUEOUS ACRYLIC ACID SOLUTION

TECHNICAL FIELD

The present invention relates to a process for producing acrylamide from acrylonitrile by the action of a microorganism-derived enzyme, nitrilehydratase. Acrylamide is used in a variety of fields as an industrially important substance. For example, acrylamide polymers are widely used in applications such as a coagulant for wastewater treatment, a paper strong agent, an oil collecting agent and the like.

BACKGROUND ART

Acrylamide has been conventionally produced industrially by hydrating acrylonitrile corresponding thereto using copper in the reduced state as a catalyst. Recently, a method using a microbial catalyst instead of a copper catalyst has been developed, and a part of this method is in actual use. A biocatalytic method using a microbial catalyst or the like has promise as an industrial production method, because the method has moderate reaction conditions and yields almost no by-product, so that an extremely simple process can be designed for this method. Thus, many microorganisms having an enzyme (enzyme name: nitrilehydratase) capable of catalyzing (converting) acrylonitrile into acrylamide by hydration have been found so far.

Examples of these microorganisms include microbial strains belonging to the genera *Bacillus, Bacteridium, Micrococcus, Brevibacterium* [see JP Patent Publication (Kokoku) No. 62-21519 B (1987) for the above microorganisms], *Corynebacterium* and *Nocardia* [see JP Patent Publication (Kokoku) No. 56-17918 B (1981) for the above microorganisms], *Pseudomonas* [see JP Patent Publication (Kokoku) No. 59-37951 B (1984)], *Rhodococcus* and *Microbacterium* [see JP Patent Publication (Kokoku) No. 4-4873 B (1992) for the above microorganisms], *Rhodococcus rhodochrous* [see JP Patent Publication (Kokoku) No. 6-55148 B (1994)], and *Rhodococcus* [see JP Patent Publication (Kokoku) No. 7-40948 B (1995)].

Examples of a process for producing acrylamide using the above microorganism as a microbial catalyst include those of JP Patent Publication (Kokai) Nos. 11-123098 A (1999) and 7-265091 A (1995), and JP Patent Publication (Kokoku) No. 56-38118 B (1981). An example of the reaction method is that of JP Patent Publication (Kokai) No. 11-89575 A (1999).

Further, a variety of studies have been conducted for improving enzyme activity or suppressing a decrease (deactivation of) in enzyme activity during reaction. Examples of such a study include a process which involves performing reaction at a low temperature, 15° C. below freezing point [see JP Patent Publication (Kokoku) No. 56-38118 B (1981)], a process which involves sequentially supplying a substrate at a low concentration from multiple supply openings [see JP Patent Publication (Kokoku) No. 57-1234 B (1982)], a process which involves treating microorganisms or the treated product thereof with an organic solvent [see JP Patent Publication (Kokai) No. 5-308980 A (1993)] a process which involves performing reaction under the presence of higher unsaturated fatty acid [see JP Patent Publication (Kokai) No. 7-265090 A (1995)], and a process which involves subjecting microbial cells to cross-linking treatment with glutaraldehyde or the like [see JP Patent Publication (Kokai) Nos. 7-265091 A (1995) and 8-154691 A (1996)].

In the meantime, for washing a microbial catalyst, the generally known methods involve washing using a physiological saline, a buffer such as an aqueous solution of phosphate or Tris hydrochroride to suppress a decrease in enzyme activity. However, there is no report on the washing of a microbial catalyst wherein the effects of wash components on the physical properties of acrylamide polymers and the storage stability of monomers have been considered.

As described above, a process for producing acrylamide using a microbial catalyst has promise as an industrial production process, because the process employs moderate reaction conditions and yields almost no by-product, so that no purification is required and an extremely simple process may be designed.

Although the above production processes yield no by-product upon enzyme reaction, they have a drawback such that when a microbial catalyst to be used is washed, contamination of impurities derived from the wash affects the physical properties of acrylamide polymers and the storage stability of acrylamide monomers. To address the problem, purification such as crystallization, ion exchange, or distillation can be performed. With these purification processes, however, an outstanding characteristic of a production process using a microbial catalyst, that is, to yield almost no by-product upon reaction, cannot be utilized. Moreover, the use of these processes is also unfavorable in terms of energy and environmental problems.

SUMMARY OF THE INVENTION

As a result of intensive studies to address the above problems, we have completed the present invention by finding that acrylamide with improved physical properties of acrylamide polymers and improved storage stability of acrylamide monomers can be produced by using a microbial catalyst washed with an aqueous acrylic acid solution in a process for producing acrylamide from acrylonitrile using a microbial catalyst having a microorganism-derived enzyme, nitrilehydratase.

In other words, the present invention is a process for producing acrylamide using a microbial catalyst that converts acrylonitrile to acrylamide, which uses the microbial catalyst having been washed with an aqueous acrylic acid solution.

The microbial catalyst that can be used in the present invention may be any catalyst as long as it is prepared from microorganisms having catalytic activity (nitrilehydratase activity) to convert acrylonitrile to acrylamide. Preferred examples of such microbial species include those belonging to the genus *Bacillus*, genus *Bacteridium*, genus *Micrococcus*, genus *Brevibacterium*, genus *Corynebacterium*, genus *Nocardia*, genus *Pseudomonas*, genus *Microbacterium*, genus *Rhodococcus*, genus *Achromobacter*, and genus *Pseudonocardia*. One of or a combination of these microorganisms can be used.

Further, a transformant that may be used herein is prepared by obtaining a nitrilehydratase gene derived from the above microorganism, and then introducing the gene directly, or the artificially improved gene, into a freely chosen host.

Preferred examples of the above transformant include *Escherichia coli* MT10770 (FERM P-14756) (JP Patent Publication (Kokai) No. 8-266277 A (1996)) that has been transformed with nitrilehydratase of the genus *Achromo*- bacter, *Escherichia coli* MT10822 ((FERM BP-5785) (JP Patent Publication (Kokai) No. 9-275978 A (1997)) that has been transformed with nitrilehydratase of the genus *Pseudonocardia*, or microorganisms transformed with nitrile-hydratase (JP Patent Publication (Kokai) No. 4-211379 A (1992) of the genus *Rhodococcus rhodochrous*.

The above microorganisms can be cultured by any method that is appropriate for a given microbial species.

In the present invention, the microbial catalyst that is prepared from microorganisms refers to a culture solution obtained by culturing microorganisms, cells obtained by a harvesting process or the like, cells disrupted by ultrasonication or the like, or those prepared after cell disruption including a crude enzyme, a partially-purified enzyme or a purified enzyme. If necessary, these microbial catalysts may be immobilized on carriers such as polyacrylamide gel, alginate, carrageenan or ion exchange resin. A mode to use the microbial catalyst may be appropriately selected depending on enzyme stability, production scale and the like.

The term "washing" in the present invention refers to the washing of microbial cells that have been cultured and/or microbial catalysts to be used in a reaction. Thus, both microbial cells that have been cultured and microbial catalysts to be used in a reaction may be washed with acrylic acid, or only the microbial catalysts to be used in a reaction may be washed with acrylic acid. For example, a microbial catalyst to be used in a reaction may be washed once with water, a buffer or the like, and then washed with acrylic acid before the reaction. Microbial catalysts may be washed with acrylic acid immediately before the reaction.

Further, any washing method can be employed. Examples of such a method that can be illustrated herein include a method which involves repeated washing and centrifugation, and a washing method using a hollow fiber membrane. Further, immobilized microbial catalysts can be washed by repeating agitation and precipitation of the immobilized catalysts in a wash and the removal of supernatant.

Any washing method and any number of washing can be appropriately set in consideration of washing efficiency, enzyme stability and the like.

The concentration of acrylic acid to be used for washing is preferably between 0.01% by mass and 10% by mass in an aqueous acrylic acid solution. More preferably, the concentration is between 0.05% by mass and 1% by mass, and most preferably is 0.1% by mass.

When the concentration of acrylic acid is 0.01% by mass or less, the duration of washing and the number of washing increase, so as to make the procedures complex. Furthermore, such increased number of washing cause cell disruption during washing, collapsed immobilized cells and the like. 10% by mass or more of the concentration is unfavorable because it causes a decrease in enzyme activity, and is also unfavorable economically.

The pH of an aqueous acrylic acid solution is adjusted using sodium hydroxide, ammonia or the like. Preferably the pH of the solution used herein is adjusted to be between 5 and 11, more preferably between 6 and 10, and most preferably to be 7.

Microbial catalysts prepared as described above can be used as microbial catalysts in a state of suspension or dispersal in an aqueous acrylic acid solution, or in a state of being subjected to solid-liquid separation.

BEST MODE OF CARRYING OUT THE INVENTION

The present invention will be described more specifically by the following examples. These examples are not intended to limit the scope of the present invention.

EXAMPLE 1

(1) Process for Preparing Cultured and Washed Microbial Cells

*Rhodococcus rhodochrous* J-1 (FERM BP-1478) having nitrilehydratase activity (JP Patent Publication (Kokoku) No. 6-55148 B (1994)) was cultured in a medium (pH 7.0) containing 2% by mass of glucose, 1% by mass of urea, 0.5% by mass of peptone, 0.3% by mass of yeast extract, and 0.05% by mass of cobalt chloride in a 30 L jar fermenter (Takasugi Seisakusho) at 30° C. for 60 hours aerobically.

20 liters of the solution cultured as described above were filtered by circulation through a cross flow type hollow fiber membrane module. The cultured cells were washed by sequentially supplying 0.7% by mass of phosphate buffer (pH 7.0) in a volume corresponding to the volume of the filtrate to the culture solution, thereby obtaining washed microbial cells.

(2) Preparation of Microorganism-Immobilized Carriers

To 500 g of the washed cell suspension (20% by mass when converted into dry cell weight) obtained in (1), 500 g of a monomer mixture solution containing acrylamide, methylene bisacrylamide and 2-dimethylaminopropyl-methacrylamide with a concentration of 20%, 2% and 2% by mass, respectively, was added, so as to perform suspension well. 5% by mass (2 g) of ammonium persulfate and 50% by mass (2 g) of N,N,N,N-tetramethylethylenediamine were added to the suspension for polymerization and gelatinization. The product was cut into an approximately 1-mm cube, thereby obtaining microorganism-immobilized carriers.

The microorganism-immobilized carrier obtained by the above method was subjected to 20 cycles of a procedure, each cycle consisting of the following steps: (1) suspension and agitation in a 0.1% by mass aqueous sodium acrylate solution (pH 7.0), (2) still standing and precipitation, and (3) disposal of supernatant.

(3) Amidation Reaction 3200 g of a 0.2 g/L aqueous sodium acrylate solution was put in a separable flask with an internal volume of 5 liters. To the aqueous acrylic acid solution, 3 g of the immobilized microorganisms prepared in (2) was added. The solution was agitated while maintaining pH 7.0 and a temperature of 20° C.

To this solution, acrylonitrile was sequentially fed for keeping the concentration of acrylonitrile at 2% by mass, and then an accumulation reaction was performed until the acrylamide concentration became 50% by mass.

After the end of the reaction, the solution was filtered through a membrane filter with an aperture of 0.45 μm, so as to remove the catalyst.

(4) Method for Evaluating the Physical Properties of Polymer

The 20% by mass of acrylamide obtained in Example 1(3) was dissolved in 80% by mass of water. After the pH was adjusted to 8.0, the solution was transferred into a Dewar flask, and then the air within the system was replaced by nitrogen. Then, 0.0004% of ammonium persulfate, 0.0004% of iron sulfate, and 0.01% of 4,4'-azobis-(4-cyanovaleric acid) were added to perform polymerization. The thus obtained water-containing gelatinous polymers were shredded into particles with a diameter of several mm using a meat mincer. The particles were then dried at 80° C. for 10 hours, and then disrupted to have a particle size of 2 mm or less using a Wiley grinder, thereby obtaining polymer powder.

The thus obtained polymer powder was prepared to have a concentration of 0.2% with 500 g of water. The solution was agitated at room temperature for 4 hours and then dissolved. The Brookfield viscosity (type B viscometer, the number of rotation of a rotor: 30 rpm, and Rotor No. 1) was then measured. Then, the solution was filtered through a 80-mesh woven metal wire, and then the mass of insoluble matters that had remained on the wire after washing with water was measured.

(5) Method for Evaluating Monomer Storage Stability 50 g of the 50% acrylamide monomer aqueous solution obtained in Example 1 (3) and iron test pieces were put in a 100 ml polyethylene-made bottle, and then the bottle was closed with a cap to avoid evaporation. This bottle was stored in a high temperature box at 50° C., and then the stability was determined based on the presence or absence of polymerized products.

The results of Example 1 (4) and (5) are shown in Table 1 and Table 2.

COMPARATIVE EXAMPLE 1

Comparative example 1 was performed similarly to Example 1 except for using a 0.7% phosphate buffer (pH 7.0) instead of 0.1% by mass of aqueous sodium acrylate solution (pH 7.0) in the step of preparing microorganism-immobilized carriers in Example 1 (2). The results are shown in Table 1 and Table 2.

TABLE 1

Physical properties of polymer

| | Time for polymerization [min.] | Viscosity [mPa · s] | Insoluble matter [g] |
|---|---|---|---|
| Example 1 | 17 | 44 | 0 |
| Comparative example 1 | 74 | 150 | 290 |

TABLE 2

Storage stability

| | Days of storage [day] |
|---|---|
| Example 1 | >10 |
| Comparative example 1 | <1 |

All publications, patents and patent applications cited herein are incorporated herein by reference in their entirety.

INDUSTRIAL APPLICABILITY

As described in detail above, the use of a microbial catalyst that has been washed with acrylic acid when acrylamide is produced using a microbial catalyst makes it possible to obtain acrylamide with high storage stability and good quality.

The invention claimed is:

1. A process for producing acrylamide comprising washing a microbial catalyst comprising a microorganism having nitrile hydratase activity with a solution consisting of acrylic acid and water, and then contacting the washed microbial catalyst with acrylonitrile.

2. The process for producing acrylamide according to claim 1, wherein the microbial catalyst is prepared from at least one microorganism selected from the group consisting of the genus *Bacillus*, genus *Bacteridium*, genus *Micrococcus*, genus *Brevibacierium*, genus *Corynebacterium*, genus *Nocardia*, genus *Pseudomonas*, genus *Microbacterium*, genus *Rhodococcus*, genus *Achromobacter*, and genus *Pseudonocardia*.

3. The process for producing acrylamide according to claim 1, wherein the concentration of acrylic acid in the aqueous acrylic acid solution is between 0.01% by mass and 10% by mass.

4. The process for producing acrylamide according to claim 1, wherein the pH of the aqueous acrylic acid solution is between 5 and 11.

5. The process for producing acrylamide according to claim 2, wherein the concentration of acrylic acid in the aqueous acrylic acid solution is between 0.01% by mass and 10% by mass.

6. The process for producing acrylamide according to claim 2, wherein the pH of the aqueous acrylic acid solution is between 5 and 11.

7. The process for producing acrylamide according to claim 3, wherein the pH of the aqueous acrylic acid solution is between 5 and 11.

8. The process according to claim 1, wherein the microbial catalyst is an unimmoblized microorganism comprising a nitrile hydratase gene.

* * * * *